United States Patent
Hebestreit et al.

(10) Patent No.: US 11,002,726 B2
(45) Date of Patent: May 11, 2021

(54) TEST ELEMENT ANALYSIS SYSTEM

(71) Applicant: Roche Diagnostics Operations, Inc., Indianapolis, IN (US)

(72) Inventors: Kai Hebestreit, Heidelberg (DE); Sylvia Saecker, Mannheim (DE); Klaus Thome, St. Leon-Rot (DE); Werner Heidt, Darmstadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 56 days.

(21) Appl. No.: 16/106,608

(22) Filed: Aug. 21, 2018

(65) Prior Publication Data
US 2019/0004026 A1 Jan. 3, 2019

Related U.S. Application Data

(63) Continuation of application No. PCT/EP2017/055298, filed on Mar. 7, 2017.

(30) Foreign Application Priority Data

Mar. 8, 2016 (EP) .................... 16159142

(51) Int. Cl.
*G01N 33/487* (2006.01)
*A61B 5/145* (2006.01)
(Continued)

(52) U.S. Cl.
CPC ....... *G01N 33/4875* (2013.01); *A61B 5/1477* (2013.01); *A61B 5/14532* (2013.01); *G01N 27/3273* (2013.01); *A61B 2562/0295* (2013.01)

(58) Field of Classification Search
CPC .. G01N 33/48; G01N 33/487; G01N 33/4875; G01N 33/49
See application file for complete search history.

(56) References Cited

U.S. PATENT DOCUMENTS 5,351,396 A 10/1994 Sawada et al.
5,409,762 A 4/1995 Ozaki et al.
(Continued)

FOREIGN PATENT DOCUMENTS

CN 102418078 A 4/2012
DE 4305058 A1 8/1994
(Continued)

OTHER PUBLICATIONS

Hydes, Paul C., Electrodeposited Ruthenium as an Electrical Contact Material A Review of Its Properties and Economic Advantages, Platinum Metals Review, 1980, pp. 50-55, vol. 24, No. 2.
(Continued)

*Primary Examiner* — Walter L Lindsay, Jr.
*Assistant Examiner* — Andrew V Do
(74) *Attorney, Agent, or Firm* — Roche Diagnostics Operations, Inc.

(57) ABSTRACT

A test element analysis system for an analytical examination of a sample, in particular of a body fluid, is disclosed. The test element analysis system comprises an evaluation device with a test element holder for positioning a test element containing the sample and a measuring device for measuring a change in a measuring zone of the test element, the change being characteristic for an analyte. The test element holder contains contact elements with contact surfaces which allow an electrical contact between contact surfaces of the test element and the contact surfaces of the test element holder. The contact surfaces of the contact elements of the test element holder are provided with an electrically conductive surface containing metallic ruthenium.

9 Claims, 3 Drawing Sheets

(51) Int. Cl.
   *G01N 27/327*   (2006.01)
   *A61B 5/1477*   (2006.01)

(56) References Cited

U.S. PATENT DOCUMENTS

| | | | |
|---|---|---|---|
| 6,029,344 | A | 2/2000 | Khandros et al. |
| 6,134,461 | A | 10/2000 | Say et al. |
| 8,673,213 | B2 | 3/2014 | Augstein et al. |
| 8,735,737 | B2 * | 5/2014 | Ihara ............... H01R 12/57 |
| | | | 174/261 |
| 2002/0157948 | A2 | 10/2002 | Liamos et al. |
| 2004/0038072 | A1 | 2/2004 | Miura |
| 2007/0202007 | A1 | 8/2007 | Augstein et al. |
| 2008/0229808 | A1 | 9/2008 | Lee |

FOREIGN PATENT DOCUMENTS

| | | |
|---|---|---|
| EP | 0074630 A2 | 3/1983 |
| EP | 1725881 B1 | 11/2006 |
| JP | 2011-123074 A | 6/2011 |
| JP | 2015-137421 A | 7/2015 |
| WO | 2005/088319 A2 | 9/2005 |
| WO | 2014/198428 A1 | 12/2014 |

OTHER PUBLICATIONS

International Search Report dated May 12, 2017, in Application No. PCT/EP2017/055298, 3 pp.

* cited by examiner

TEST ELEMENT ANALYSIS SYSTEM

CROSS-REFERENCE TO RELATED APPLICATIONS

This application is a continuation of International Patent Application No. PCT/EP2017/055298, filed 7 Mar. 2017, which claims the benefit of European Patent Application No. 16159142.5, filed 8 Mar. 2016, the disclosures of which are hereby incorporated by reference in their entirety.

TECHNICAL FIELD

The present disclosure relates to a test element analysis system for the analytical examination of a sample and, in particular, a body fluid of humans or animals, and a method for manufacturing a test element analysis system.

BACKGROUND

Test element analysis systems are commonly used especially in medical diagnostics for analyzing body fluids such as blood or urine. The sample to be examined is firstly applied to a test element. Here the process steps that are required to detect the analyte which are usually chemical, biochemical, biological or immunological detection reactions or physical interactions take place which result in a characteristic and measurable change of the test element especially in the area of a measuring zone of the test element. In order to determine this characteristic change, the test element is inserted into an evaluation device which determines the characteristic change of the test element and provides it in the form of a measured value for display or further processing.

Test elements are often designed as test strips which are essentially composed of an elongate support layer, usually made of a plastic material, and a measuring zone with a detection layer containing detection reagents and, if necessary, other auxiliary layers such as filtration layers. The test elements of the present disclosure additionally contain contact surfaces, also denoted as contact areas, which can be used to make an electrical contact between the test element and the evaluation device. In the case of electrochemical assay methods conductor paths and electrodes are located on the test element. Even test elements which do not use methods of electrochemical analysis can have electrically conducting contact surfaces for example in order to transfer calibration data or batch information that are stored on the test element to the evaluation instrument.

The accompanying evaluation devices have test element holders with special contact elements which make an electrically conducting contact between the test element and the measuring and evaluation electronics of the evaluation instrument. These contact elements are usually in the form of electrical plug connections with metallic spring elements which are often provided with a noble metal surface usually of gold or platinum. The test strips are inserted into the test element holder for the measurement during which the contact surfaces of the contact elements of the evaluation instrument are moved across the electrodes of the test elements. In an end position the contact surface of the contact elements of the evaluation instrument is then in contact with the contact surface of the test element. An electrically conducting connection is made between the test element and evaluation instrument by a pressing force that is in particular defined by the shape and spring force of the contact element. This should in particular ensure that the transition resistance between the contact surface of the contact element of the evaluation instrument and the contact surface of the test element is as low and constant as possible to enable an exact and reproducible signal transfer. A constant and reproducible transition resistance is especially important in order to still obtain exact measurement results even after multiple test elements have previously been plugged in and thus to obtain a high and reproducible measurement accuracy especially with regard to the fact that such test element analytical systems are often used for many years or many tens of thousands of subsequent test strip insertions are carried out. This is of major importance especially in the clinical field where such test systems often have to handle a high throughput.

A major advantage of pluggable contact devices is the ability to easily join and separate the electrical connection so that the test element and evaluation device can be stored and used independently of one another. Since the contact surfaces should, on the one hand, ensure that the transfer of electrical current is as optimal as possible which requires a certain contact pressure, but, on the other hand, joining the contact connection and in particular repeated joining and separating the contact connection puts a great strain on the connection, the contact surfaces of the evaluation instruments are often provided with a layer of noble metal for example by plating or galvanizing with gold, silver, platinum or palladium. The often high mechanical strain on the contact surfaces especially due to abrasion, deposition or scratching of the contact surfaces is thus also a problem because a certain contact pressure has to be ensured for a reliable electrical contact and a certain insertion path of the test element is necessary for mechanical reasons and in particular to ensure guidance when plugging in and mechanical stability in the plugged state. It is very important that the contact surfaces are as resistant as possible to external influences in order to make a very secure and reliable contact between the contact surfaces of an electrical contact connection and with regard to having the lowest possible contact resistances. In this connection, the external influences can be of a chemical, physical or mechanical type. Thus, especially during the plugging process, the two contact surfaces rub against one another resulting in a very high mechanical strain. Corrosion effects and especially crevice corrosion also have an adverse effect on the contact security and contact resistance. Another problem of such test element analytical instruments is that the support material of the test elements that are used often consists of an elastic and relatively soft plastic foil on which the contact surfaces and electrodes are placed so that this structure on a relatively soft base material can have disadvantages for an exact contacting.

A major disadvantage of noble metal-noble metal pairs for contact surfaces of such plug-in connections is that, even irrespective of their geometry and/or the pressing force, the metal surfaces are very often damaged when the contact surfaces are joined and thus electrical contact problems occur. Such contact problems often manifest themselves in that the transition resistances between the contact elements of the evaluation device and contact surfaces of the test element become very high or in an extreme case there may be no longer any electrical contact between the components of the contact connection. When observed under the microscope, the picture of damage that often results, especially in the case of flat contacts such as conductor paths or electrodes, is characterized by a major change in the thickness of the metal layer of these contact surfaces after the insertion. Thus the metal layer of the electrodes is strongly deformed in some areas by the second contact surface that moves across it, in particular in the form of grooves, ridges and scratches. This pattern of damage occurs especially when the electrodes are mounted on relatively soft base materials. These deformations may become so large that the metal layer is completely stripped away in some areas by the second contact surface moving across it. In this case, electrical contact between the test element and evaluation device is no longer possible. Such deformations of metal layers which serve as contact surfaces manifest themselves as non-defined and considerably increased transition resistances or in the complete lack of an electrical contact. Such contact elements are therefore unsuitable for use in analytical systems which are intended to ensure a reproducible determination of analyte over a long period of use.

In U.S. Pat. No. 8,673,213 B2, EP 1 725 881 B1, WO 2005/088319 A2 and "Untersuchung and Optimierung von Kontaktsystemen in elektrochemischen Messgeräten", Dissertation of S. Riebel, 2006 a test element analysis system with contact surfaces coated with a hard material is disclosed. The documents disclose a test element analytical system for the analytical examination of a sample, especially a body fluid. The system comprises at least one test element with one or more measuring zones and contact areas located on the test element, in particular electrodes or conductor paths. The sample to be examined is brought into the measuring zone to carry out an analysis in order to determine a characteristic measured quantity for the analysis. The system further comprises an evaluation instrument with a test element holder for positioning the test element in a measuring position and a measuring device for measuring the characteristic change. The test element holder contains contact elements with contact areas which enable an electrical contact between the contact areas of the test element and the contact areas of the test element holder. One of these contact areas is provided with an electrically conductive hard material surface. Hard materials are understood as materials which, due to their specific binding properties, are very hard and in particular have a Vickers hardness of greater than about 1000 kp/mm and include in particular carbides, borides, nitrides and silicide, high-melting metals such as chromium, zirconium, titanium, tantalum, tungsten or molybdenum including mixed crystals and complex compounds thereof.

Despite the improvements due to the use of hard materials, a need for even more robust and reliable contacts exists. Contact surfaces coated with hard materials show abrasion of materials at contact surfaces. In particular, contact surfaces coated with a hard material may exhibit deviations from form and surface quality of the contact surface over lifetime. Contacts with contact surfaces coated with hard materials may be highly sensitive to form and surface quality. Thus, quality problems may occur when using contact surfaces coated with a hard material. Contact surfaces coated with hard material may exhibit a drift in transition resistance over lifetime, e.g., after multiple plugging operations, in particular after several tens of thousands plugging operations. In addition, contact surfaces coated with hard materials may show a run-in behavior, also denoted as running-in characteristics, with respect to transition resistance. Furthermore, manufacturing of contact surfaces coated with hard materials may be complex, requires several processes and thus, may be expensive. In addition, process reliability of manufacturing of contact surfaces coated with hard materials may be insufficient. Reel-to-reel processes may not be possible.

Such contacts having ruthenium dioxide may be disadvantageous because the application of ruthenium dioxide may be complex and expensive. In particular, a galvanic coating may be not possible and, thus, manufacturing of ruthenium dioxide contacts may be expensive and non economic.

There is a need for reliable and defined electrical connection between the contact surfaces of a contact element of a evaluation device and the contact surfaces of a test element over a long time period, especially under high mechanical strain and even after numerous contacting operations.

BRIEF SUMMARY

It is against the above background that the embodiments of the present disclosure provide certain unobvious advantages and advancements over the prior art. In particular, the inventors have recognized a need for improvements in test element analysis systems and methods for manufacturing.

Although the embodiments of the present disclosure are not limited to specific advantages or functionality, it is noted that the present disclosure ensures reliable and defined electrical connection between the contact surfaces of a contact element of a evaluation device and the contact surfaces of a test element over a long time period, especially under high mechanical strain and even after numerous contacting operations.

In accordance with one embodiment of the present disclosure, a test element analysis system for an analytical examination of a sample is provided, comprising: an evaluation device with a test element holder for positioning a test element containing the sample and a measuring device for measuring a change in a measuring zone of the test element, the change being characteristic for an analyte, wherein the test element holder contains contact elements with contact surfaces which allow an electrical contact between contact surfaces of the test element and the contact surfaces of the test element holder. The contact surfaces of the contact elements of the test element holder are provided with an electrically conductive surface containing metallic ruthenium. The test element holder comprises at least one metal part containing the contact elements with the contact surfaces, wherein the metal part is made of at least one conductive material other than ruthenium, and wherein the conductive material, in the region of the contact elements, is fully or partially coated with ruthenium.

In accordance with another embodiment of the present disclosure, a method for manufacturing a test element analysis system according to the embodiment above is provided, the method comprising the following steps: a) providing the contact elements having the electrically conductive surface containing metallic ruthenium; and b) electrically connecting the contact elements with at least one electronic component of the evaluation device, wherein step a) comprises providing at least one metal part containing the contact elements with contact surfaces, wherein the metal part is made of at least one conductive material other than ruthenium, and wherein step a) further comprises fully or partially coating the conductive material, in the region of the contact elements, with ruthenium.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1:
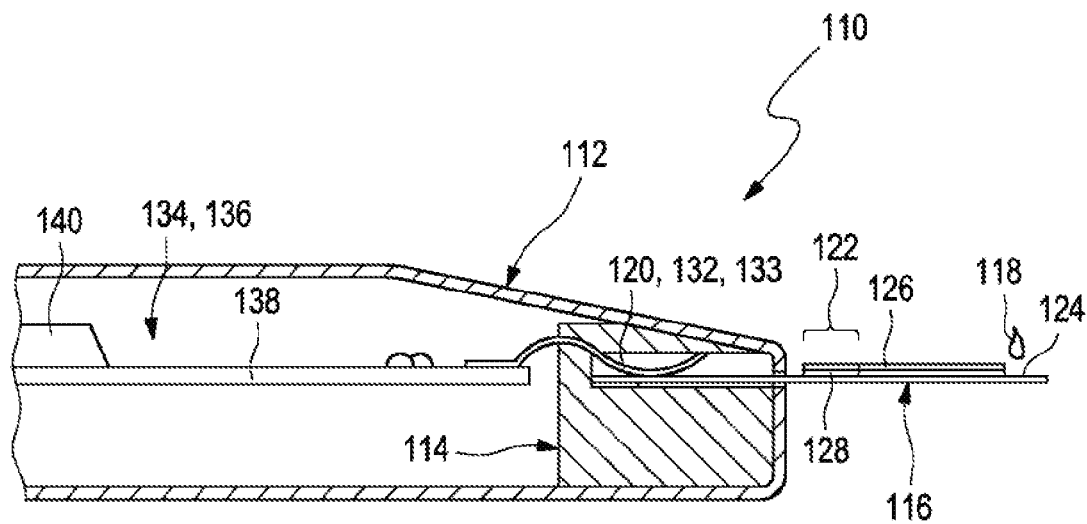
FIG. 1 shows a partial sectional view of a test element analysis system according to an embodiment of the present disclosure.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "typically", "more typically", "particularly", "more particularly", "specifically", "more specifically" or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in such way with other optional or non-optional features of the disclosure.

In a first embodiment of the present disclosure, a test element analysis system for an analytical examination of a sample, in particular of a body fluid, is disclosed. The test element analysis system comprises an evaluation device with a test element holder for positioning a test element containing the sample and a measuring device for measuring a change in a measuring zone of the test element. The change is characteristic for an analyte. The test element holder contains contact elements with contact surfaces which allow an electrical contact between contact surfaces of the test element and the contact surfaces of the test element holder. The contact surfaces of the contact elements of the test element holder are provided with an electrically conductive surface containing metallic ruthenium.

As generally used within the present disclosure, the term "test element analysis system" may refer to an arbitrary device configured for an analytical examination of a sample. The test element analysis system may be configured for conducting at least one analysis, in particular a medical analysis, of a test element which may contain the sample. The term "analyte" encompasses atoms, ions, molecules and macromolecules, in particular biological macromolecules such as nucleic acids, peptides and proteins, lipids, metabolites, cells and cell fragments. In the sense of the present application, the sample used for the analytical examination is understood as an unchanged medium containing the analyte as well as an already changed medium containing the analyte or substances derived therefrom. The change in the original medium can in particular be carried out in order to lyse the sample, to process the analyte or to carry out detection reactions. Typical samples are liquids, in particular a bodily fluid. Liquids can be pure liquids and homogeneous or heterogeneous mixtures such as dispersions, emulsions or suspensions. In particular, the liquids can contain atoms, ions, molecules and macromolecules, in particular biological macromolecules such as nucleic acids, peptides and proteins, lipids, metabolites or also biological cells or cell fragments. Typical liquids to be examined are body fluids such as blood, plasma, serum, urine, cerebrospinal fluid, lachrymal fluid, cell suspensions, cell supernatants, cell extracts, tissue lysates or such like. Liquids can, however, also be calibration solutions, reference solutions, reagent solutions or solutions containing standardized analyte concentrations, so-called standards. As generally used within the present disclosure, the term "analytical examination or determination of analytes" is understood as a qualitative as well as a quantitative detection of the analyte. In particular, it is understood as a determination of the concentration or amount of the respective analyte where the sole determination of the absence or presence of the analyte is also regarded as an analytical examination.

Test element analytical systems are typically used in analytical and medical laboratories. However, the disclosure is also directed towards fields of application in which the analysis is carried out by the patients themselves in order to continuously monitor their state of health (home monitoring). This is of particular medical importance for example for monitoring diabetics who have to determine the concentration of glucose in their blood several times daily or patients who take anti-coagulant drugs and therefore have to determine their coagulation status at regular intervals. For such purposes the evaluation instruments should be as light and small as possible, and be battery-operated and robust.

Such test element analytical systems are described for example in DE 43 05 058, the disclosure of which is hereby incorporated herein by reference.

Test elements are frequently in the form of test strips which are essentially composed of an elongate support layer usually consisting of a plastic material and a measuring zone with a detection layer containing the detection reagents and possibly other auxiliary layers such as filtration layers. In addition, test elements can contain other structural elements, for example dosing and transport devices for the sample such as channels or fleeces, positioning devices such as cut-outs to ensure an exact positioning of the test element and thus an exact measurement in the evaluation device or coding elements for example in the form of a bar code or an electronic component which are used to transfer specific parameters of the test element such as calibration data or batch information to the evaluation device.

Test elements usually contain reagents in the measuring zone whose reaction with the sample and in particular with the analytes contained in the sample results in a characteristic and measurable change of the test element which can be determined by the evaluation instrument which is part of the system. The measuring zone can optionally contain other auxiliary substances. The measuring zone can also contain only parts of the reagents or auxiliary substances. In other cases it is possible that the detection reactions to determine the analyte do not occur directly in the measuring zone but rather the reagent mixture is only transferred to the measuring zone for measurement after the detection reactions are completed. One skilled in the art of analytical test elements or diagnostic test carriers is very familiar with suitable reagents and auxiliary agents for carrying out analyte-specific detection reactions. In the case of analytes that are detected analytically, the measuring zone can for example contain enzymes, enzyme substrates, indicators, buffer salts, inert fillers and such like. In addition to detection reactions which result in color changes, a person skilled in the art also knows other detection principles which can be realized with the described test element such as electrochemical sensors or chemical, biochemical, molecular biological, immunological, physical, fluorimetric or spectroscopic detection methods. The subject-matter of the present disclosure can be used in all these detection methods. This applies particularly to electrochemical analytical methods in which, as a result of an analyte-specific detection reaction, a change in the measuring zone occurs that can be measured electrochemically usually as a voltage or current flow.

In addition to such analytical systems that use reagents, the subject-matter of the present disclosure can also be used in reagent-free analytical systems in which, after the test element has been contacted with the sample, a characteristic property of the sample (for example its ion composition by means of ion selective electrodes) is measured directly without further reagents. The disclosure can also be fundamentally used for such analytical systems.

As used herein, the term "evaluation device" generally refers to an arbitrary device configured to perform an analysis of the sample. The evaluation device comprises a test element holder. The term "test element holder" generally refers to an arbitrary device which is configured to receive at least one test element and to position the test element for measuring a change in the measuring zone of the test element. The evaluation device comprises a measuring device for measuring the change in the measuring zone of the test element. As used herein, the term "measuring device" refers to an arbitrary device configured to measure and/or detect at least one change in the measuring zone of the test element. The evaluation device and/or the measuring device may have at least one electronic unit having at least one electronic component. Specifically, the electronics unit may comprise at least one electronic component for performing a measurement of a change in the measuring zone of the test element, recording measurement signals of the measuring device, storing measurement signals or measurement data, transmitting measurement signals or measurement data to another device.

The evaluation device comprises a test element holder in order to position a test element in a measuring position for carrying out the measurement. In order to determine the analyte, the test element may be placed in the evaluation device which determines the characteristic change of the test element that is caused by the analyte and provides it in the form of a measured value for display or further processing. The analyte can be determined with a variety of detection methods known to a person skilled in the field of instrument analytics. In particular, optical and electrochemical detection methods can be used. Optical methods for example encompass the determination of characteristic changes in the measuring zone by measuring absorption, transmission, circular dichroism, optical rotation dispersion, refractometry or fluorescence. Electrochemical methods can in particular be based on the determination of characteristic changes in charge, potential or current in the measuring zone.

Contact surfaces are understood within the scope of the present disclosure as electrically conductive structures of the contact element or of the test element which are directly contacted in order to make an electrical contact between the test element and evaluation device. In the case of the test element they are typically electrodes and conductor paths placed thereon and especially areas of these electrodes or conductor paths which have a formed, for example flat, structure to make the electrical contact. The contact surfaces of the contact element can also be shaped, for example as flat elements, to generate the largest possible contact surfaces or areas and thus a very secure contact and low transition resistance. These contact surfaces can also have curved shapes so that the test element can be inserted as simply and gently as possible for example in the case of spring or plug-in contacts. The contact surfaces of the contact elements of the test element holder are provided with an electrically conductive surface containing metallic ruthenium.

The term "contact element" may refer to an arbitrary device configured to allow an electrical contact between contact surfaces of the test element and the contact surfaces of the test element holder. The contact elements which are components of the test element holder of the evaluation device can have a very wide variety of designs. They can for example be designed as sliding contacts, roller contacts, plug-in contacts, spring contacts, clip contacts or zero force contacts. The inventive design of the contact surfaces can be particularly advantageous for contact reliability especially for types of contact elements such as sliding contacts, plug-in contacts, spring contacts and clip contacts in which the contact surfaces of the two elements involved in the contact connection are moved past one another while being in direct contact until their final position is reached. Particularly typical embodiments of contact elements are sliding contacts, plug-in contacts, spring contacts and clip contacts. A wide variety of possible embodiments of such contact elements is described in U.S. Pat. No. 6,029,344, for example, the disclosure of which is hereby incorporated herein by reference.

The contact surfaces of the contact elements of the test element holder are provided with an electrically conductive surface containing metallic ruthenium. The electrically conductive surface may contain pure metallic ruthenium or a compound comprising metallic ruthenium. The ruthenium may be applied by galvanic coating, directly or indirectly onto the conductive material. Since pure material elements often have disadvantageous mechanical and chemical properties such as brittleness, poor elastic properties, the ruthenium surface may be formed, e.g., by galvanic coating indirectly onto a conductive material. Other deposition or coating techniques, however, may be used additionally or alternatively. The test element holder may comprise at least one metal part containing the contact elements with the contact surfaces, wherein the metal part is made of at least one conductive material other than ruthenium, wherein the conductive material, in the region of the contact elements, is fully or partially coated with ruthenium. The conductive material may comprise copper. The ruthenium may be applied by galvanic coating, directly or indirectly onto the conductive material.

Metallic ruthenium and compounds of metallic ruthenium distinguish from ruthenium dioxide. In ruthenium dioxide ruthenium and oxide are inseparable compounds and have different chemical and electrically conducting properties compared to metallic ruthenium. Contact surfaces containing metallic ruthenium are advantageous in view of contact surfaces containing ruthenium dioxide since manufacturing of ruthenium dioxide surface is complex and expensive. In particular, a galvanic coating of ruthenium dioxide is not possible.

Surprisingly, it turned out that functionality, i.e., run-in behavior and/or transition resistance, of the contact elements is essentially independent from the thickness of the ruthenium layer, particularly if the thickness of the ruthenium layer is within a range between 1 and 0.01 µm, typically between 0.6 and 0.1 µm. The thickness of the ruthenium layer may be between 1 and 0.01 µm, typically between 0.6 and 0.1 µm. For example, the thickness of the ruthenium layer may be 0.4 µm.

When applying a layer of ruthenium to the conductive material of the contact element, it may be advantageous to firstly apply one or more intermediate layers, in particular germ or protective layers, to the conductive material and subsequently apply the ruthenium layer to these layers. Application of such intermediate layers can in particular result in a good adhesion and a durable bonding between the different materials. Thus, for example, galvanic methods can be firstly used to apply layers to the conductive material which generate a particularly suitable surface for the subsequent application of the ruthenium by galvanic coating. Furthermore, it is also possible to apply protective layers which can protect the underlying conductive material from chemical and/or physical damage such as corrosion when the ruthenium surface is damaged. In addition, the electrical properties of the contact element such as the transition resistance can be influenced by a suitable selection of materials for such intermediate layers. Such intermediate layers can for example be produced by applying particles made of a suitable material. Alternatively, in order to obtain a good and durable bond between the conductive material and hard material layer, it may be also possible to provide an additional intermediate layer wherein the surface of the conductive material of the contact element is treated before coating in such a manner that it has improved coating properties. The metal part may comprise one or more contact portions electrically connected to at least one electronic component of the evaluation device, wherein the one or more contact portions remain free of ruthenium. The metal part may be a punched press-bending part or a punched deep-drawn part.

The test element analysis system may further comprise a test element with at least one measuring zone and electrically conductive contact surfaces. The test element may contain contact surfaces that are electrically conductive and by means of which an electrical contact can be made between the test element and the evaluation device. In the case of electrochemical analytical methods, conductor paths and electrodes may be located on the test element which can be used to determine electrochemical changes in the sample and also to apply external voltages and/or currents to the sample to be examined. The electrochemical analyses on the test element can occur in particular in the measuring zone between designed electrodes while the electrical measuring signals that are emitted by them or the actuating signals directed towards them are measured or applied via the conductor paths. These conductor paths can contain designed flat areas which form contact surfaces that can be used to make an electrical contact between the test element and the evaluation device. The conductor paths and contact surfaces may consist of noble metals. Test elements which do not use electrochemical analytical methods can also have electrically conductive contact surfaces. For example, it may be advantageous to mount electronic components on a test element which are used to store specific parameters of the test element such as calibration data or batch data and transfer them to the evaluation instrument. For this purpose these specific data are stored on the test element in electronic components or circuits. When the test element is introduced into the evaluation instrument, these data can be read and processed by reading electronics of the evaluation instrument.

The electrically conductive contact surfaces may comprise one or both of electrodes or conductive paths. The electrically conductive contact surfaces of the test element may be softer than ruthenium. In particular, it has turned out to be particularly advantageous when the contact surface opposite to the contact surface provided with a ruthenium surface consists of a material which has a lower hardness than the ruthenium surface of the other contact surface. The electrically conductive contact surfaces of the test element may be fully or partially made of gold. Metals are typically suitable for this and especially noble metals such as gold. Such materials are already widely used for contact surfaces especially of electrodes and conductor paths on test elements. Consequently, it is in many cases sufficient to provide the evaluation device with contact elements having ruthenium surfaces according to the disclosure, in which such conventional test elements can then be inserted. Surprisingly, it turned out that the combination of a contact surface with a ruthenium material surface and a contact surface made of a material which has a lower hardness than the material of the ruthenium surface enables a high reproducibility of the transition resistance between the test element and evaluation device to be achieved.

As outlined above, in U.S. Pat. No. 8,673,213 B2, EP 1 725 881 B1, WO 2005/088319 A2 it was found that a defined and reproducible electrical contact between the test element and evaluation is improved compared to contact areas made of a noble metal on both sides especially even after many insertions by coating a contact area with an electrically conductive hard material. But, after several plugging operations, in particular after several ten thousands plugging operations, contact surfaces coated with a hard material may be influenced and/or destroyed due to abrasion. Contact surfaces coated with hard materials may exhibit a run-in behavior with respect to transition resistance and a drift in transition resistance. Manufacturing of contact surfaces coated with hard materials may be complex, requires several processes and thus, may be expensive. In addition, process reliability of manufacturing of contact surfaces coated with hard materials may be insufficient. U.S. Pat. Nos. 6,029,344 A1, 5,409,762 A and 6,134,461 A disclose contact surfaces containing contact materials of platinum group, which comprises ruthenium, rhodium, palladium, osmium, iridium, and platinum. However, in EP 0 074 630 A2 compounds of the platinum-group metals as well as precious metals (ruthenium, rhodium, palladium, silver, osmium, iridium, platinum and gold) have been excluded due to economic reasons. Surprisingly, it was found that a contact surface containing metallic ruthenium ensures a low transition resistance between the contact surface of the test element holder and the test element, in particular less than about 50 Ohm. In addition, a high reproducibility of the transition resistance between the test element and evaluation device was found, with little scatter. Further, surprisingly, no run-in behavior was found such that reliable measurement values are ensured directly. Furthermore, functionality of the contact elements was found to be essentially independent from the thickness of the ruthenium layer. In particular, it may be possible to determine reliable measurement values even at very thin ruthenium layers. For example, reliable measurement values may be achieved even at layers thickness of 0.01 µm. Thus, durability, i.e., the amount of subsequent plugging operations, and functionality of the contact surface can be enhanced. Contact surfaces containing metallic ruthenium may be further advantageous because abrasion of the opposing softer contact surface, e.g., of gold, is further reduced and thus adhesion of the abraded particles on the ruthenium contact layer of the device can be reduced. In addition, because the application of ruthenium may be performed by galvanic coating processes, manufacturing of ruthenium contacts may be shorter, less complex and, thus, less expensive than of hard material contacts or of ruthenium dioxide contacts. Thus, process times for manufacturing can be reduced and process reliability can be enhanced.

In accordance with another embodiment of the disclosure, a method for manufacturing a test element analysis system according to the disclosure is disclosed. With respect to definitions and embodiments of the method, reference can be made to definitions and embodiments of the test element analysis described above. The method comprises the following steps: a) providing the contact elements having the electrically conductive surface containing metallic ruthenium; and b) electrically connecting the contact elements with at least one electronic component of the evaluation device. Step a) may comprise providing at least one metal part containing the contact elements with the contact surfaces, wherein the metal part is made of at least one conductive material other than ruthenium. Step a) may further comprise fully or partially coating the conductive material, in the region of the contact elements, with ruthenium.

Summarizing the findings of the present disclosure, the following embodiments are typical:

Embodiment 1: Test element analysis system for an analytical examination of a sample, in particular of a body fluid, comprising an evaluation device with a test element holder for positioning a test element containing the sample and a measuring device for measuring a change in a measuring zone of the test element, the change being characteristic for an analyte, wherein the test element holder contains contact elements with contact surfaces which allow an electrical contact between contact surfaces of the test element and the contact surfaces of the test element holder, wherein the contact surfaces of the contact elements of the test element holder are provided with an electrically conductive surface containing metallic ruthenium.

Embodiment 2: The test element analysis system according to the preceding embodiment, wherein the electrically conductive surface contains pure metallic ruthenium or a compound comprising metallic ruthenium.

Embodiment 3: The test element analysis system according to any one of the preceding embodiments, wherein the test element holder comprises at least one metal part containing the contact elements with the contact surfaces, wherein the metal part is made of at least one conductive material other than ruthenium, wherein the conductive material, in the region of the contact elements, is fully or partially coated with ruthenium.

Embodiment 4: The test element analysis system according to the preceding embodiment, wherein the conductive material comprises copper.

Embodiment 5: The test element analysis system according to any one of the two preceding embodiments, wherein the ruthenium is applied by galvanic coating, directly or indirectly onto the conductive material.

Embodiment 6: The test element analysis system according to any one of the three preceding embodiments, wherein the metal part comprises one or more contact portions electrically connected to at least one electronic component of the evaluation device, wherein the one or more contact portions remain free of ruthenium.

Embodiment 7: The test element analysis system according to any one of the four preceding embodiments, wherein the metal part is a punched press-bending part or a punched deep-drawn part.

Embodiment 8: The test element analysis system according to any one of the preceding embodiments, further comprising a test element with at least one measuring zone and electrically conductive contact surfaces.

Embodiment 9: The test element analysis system according to the preceding embodiment, wherein the electrically conductive contact surfaces comprise one or both of electrodes or conductive paths.

Embodiment 10: The test element analysis system according to any one of the two preceding embodiments, wherein the electrically conductive contact surfaces of the test element are softer than ruthenium.

Embodiment 11: The test element analysis system according to any one of the three preceding embodiments, wherein the electrically conductive contact surfaces of the test element are fully or partially made of gold.

Embodiment 12: A method for manufacturing a test element analysis system according to any one of the preceding embodiments, the method comprising the following steps:

a) providing the contact elements having the electrically conductive surface containing metallic ruthenium; and b) electrically connecting the contact elements with at least one electronic component of the evaluation device.

Embodiment 13: The method according to the preceding embodiment, wherein step a) comprises providing at least one metal part containing the contact elements with the contact surfaces, wherein the metal part is made of at least one conductive material other than ruthenium, wherein step a) further comprises fully or partially coating the conductive material, in the region of the contact elements, with ruthenium.

In order that the embodiments of the present disclosure may be more readily understood, reference is made to the following examples, which are intended to illustrate the disclosure, but not limit the scope thereof.

FIG. 1 shows a test element analysis system 110 which comprises an evaluation device 112. The evaluation device 112 has a test element holder 114 for positioning a test element 116 containing a sample 118. The test element holder 114 may be configured for positioning the test element 116 in a measuring position shown in FIG. 1. The test element 116 may be fixed in the measuring position by suitable means, for example by a spring element 120. In order to carry out a measurement, sample liquid may be brought into a measuring zone 122 of the test element 116. In the embodiment shown this occurs by applying a drop of liquid to the sample application zone 124 provided at an end of the test element 116 and transporting it from this position through a transport zone 126, for example a capillary channel, to the measuring zone 122. A reagent layer 128 may be located in the measuring zone 122 which may be dissolved by the sample liquid and reacts with its components. The reaction may result in a detectable change in the measuring zone 122. In the case of an electrochemical test element, the measured electrical quantity may be determined by means of the electrodes 130 shown in FIG. 2 that are provided in the measuring zone 122. The test element holder 114 contains contact elements 132 with contact surfaces 133 which allow an electrical contact between contact surfaces 117 of the test element 116 and the contact surfaces 133 of the test element holder 114. In the measuring position, an electrical contact may be made between the test element 116 and the contact element 132 of the test element holder 114 (FIG. 1).

The evaluation device 122 comprises a measuring device 134 for measuring a change in the measuring zone 122 of the test element 116, the change being characteristic for an analyte. The contact element 132 may be connected to measuring and evaluation electronics 136 which may be highly integrated in order to achieve a very compact construction and high degree of reliability. In the case shown they are essentially composed of a printed circuit board 138 and an integrated circuit 140. To this extent the analysis system has a conventional construction and needs no further explanation.

Figure 2:
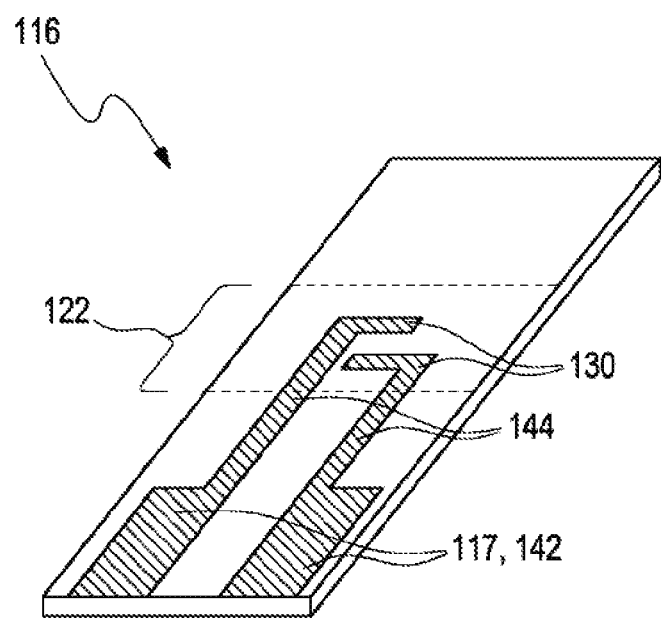
FIG. 2 shows an exemplary view of a test element.

FIG. 2 shows a partial view of an exemplary test element 116. An analyte-specific change may be detected as part of the analyte determination within the measuring zone 122. In the case shown of an electrochemical test element, a measured electrical quantity is measured by means of electrodes 130 provided in the measuring zone 122. The test element 116 may comprise electrically conductive contact surfaces 142. In particular, the contact surfaces 117 of the test element 116 may be provided with electrically conductive contact surfaces 142. The electrical signal may be passed onto the electrically conductive contact surfaces 142 via conductive paths 144. These electrically conductive contact surfaces 142 may make direct contact with the contact surfaces 133 of the contact element 132 (see FIG. 3) when the test element 116 is plugged into the test element holder 114 and thus make an electrical contact between test element 116 and evaluation device 112. The electrically conductive contact surfaces 142 of the test element 116 may be softer than the ruthenium coated contact surfaces of the evaluation device. The electrically conductive contact surfaces 142 of the test element 116 may be fully or partially made of gold. The test element 116 that is shown here is only an exemplary and minimalized embodiment of a test strip. Test elements with other arrangements of electrodes and conductor paths and with several electrodes, for example reference electrodes, and additional structures such as sample application and transport zones or reaction areas can also be used within the scope of the present disclosure.

Figure 3:
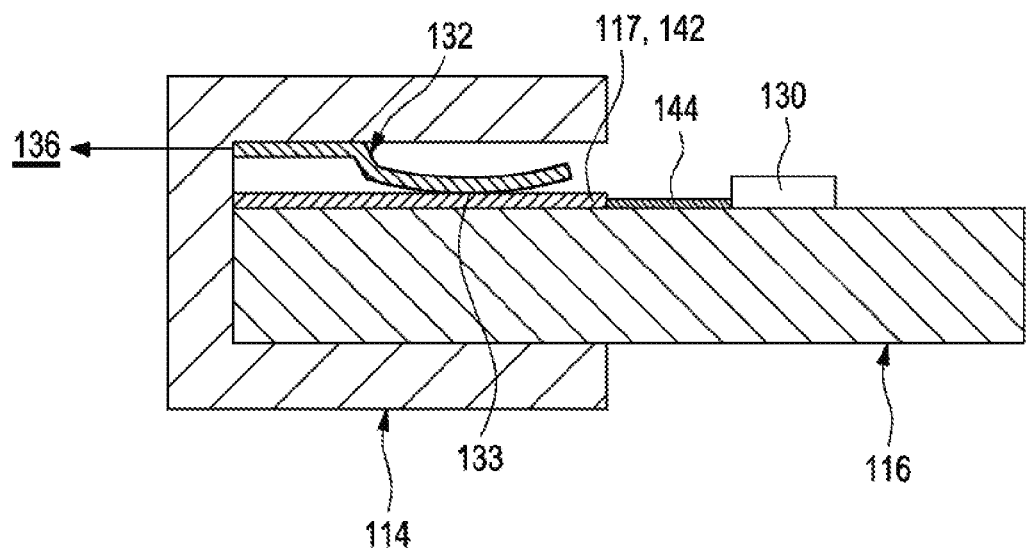
FIG. 3 shows a detailed view of a contact element according to an embodiment of the present disclosure.

FIG. 3 shows a detailed view of a contact element 132 according to an embodiment of the present disclosure. The test element 116 is introduced into the test element holder 114 by insertion. Electrical contact may be made between the contact surfaces 133 of the contact element 132 and the electrically conductive contact surfaces 142 of the test element 116. In this case, the contact element 132 is designed such that it has elastic properties and thus exerts a defined contact pressure on the test element 116. This is exhibited by a particularly typical embodiment in which the contact element 132 may ensure the electrical contacting as well as the positioning and fixing of the test element 116.

Figure 4:
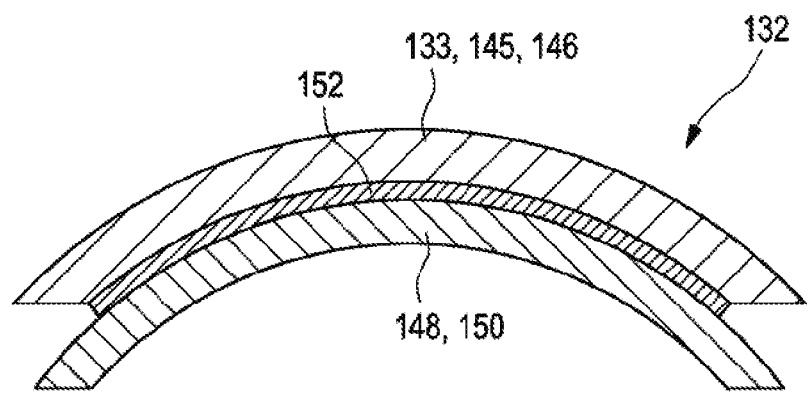
FIG. 4 shows a detailed view of a cross-section of a contact element with an electrically conductive surface containing metallic ruthenium.

FIG. 4 shows a detailed view of a cross-section of a contact element 132. The contact surfaces 133 of the contact element 132 of the test element holder 114 are provided with an electrically conductive surface 145 containing metallic ruthenium 146. The test element holder 114 may comprise at least one metal part 148 containing the contact elements 132 with the contact surfaces 133. The metal part 148 may be made of at least one conductive material 150 other than ruthenium. The conductive material 150, in the region of the contact elements 132, is fully or partially coated with ruthenium. The conductive material 150 may comprise copper. A layer of metallic ruthenium 146 may be applied to the conductive material 150 of the contact element 132, and an intermediate layer 152 may be present in this case between the two layers which in particular can be designed as a bonding or protective layer. The ruthenium may be applied by galvanic coating, directly or indirectly onto the conductive material 150. The metal part 148 may comprise one or more contact portions electrically connected to at least one electronic component of the evaluation device 112, wherein the one or more contact portions remain free of ruthenium. The metal part 148 may be a punched press-bending part or a punched deep-drawn part.

Figure 5:
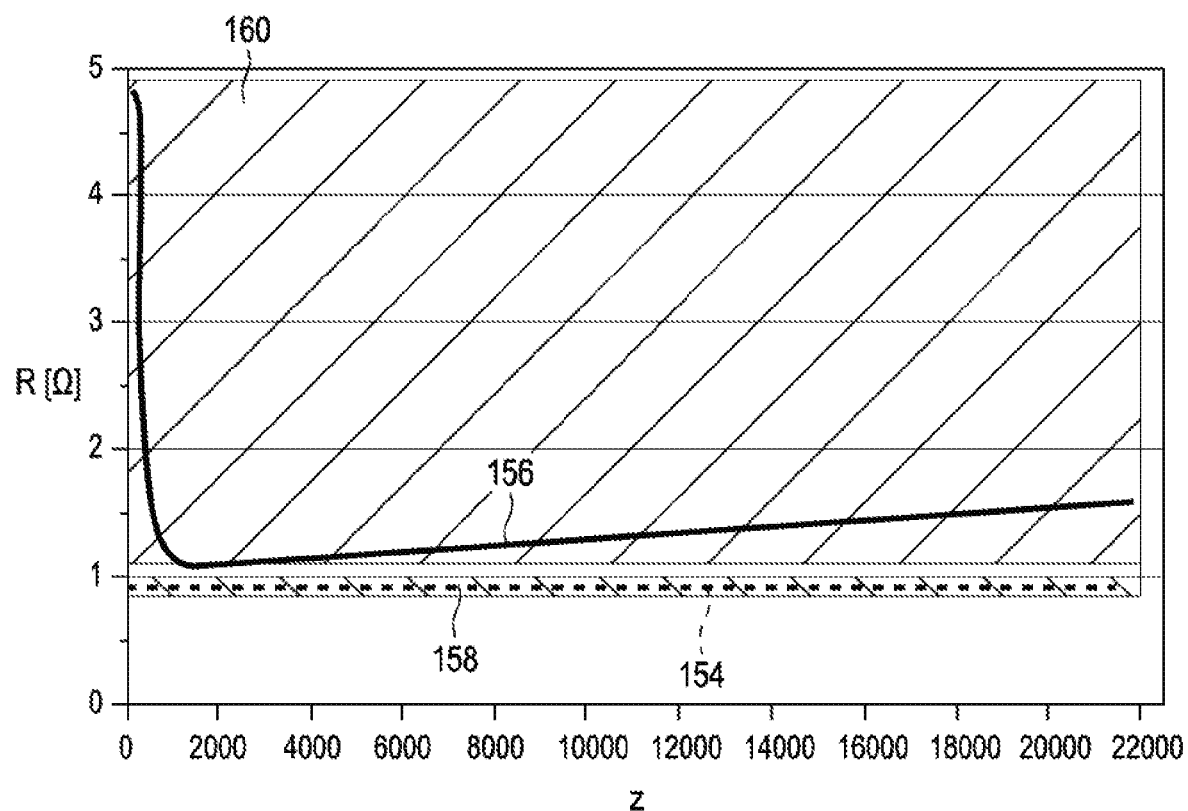
FIG. 5 shows a comparison of experimental results of an endurance test of contact elements.

FIG. 5 shows a comparison of experimental results of an endurance test of contact elements. With respect to experimental setup, reference can be made to "Untersuchung and Optimierung von Kontaktsystemen in elektrochemischen Messgeräten", Dissertation of S. Riebel, 2006, FIGS. 5.2 on page 44 and 5.4 on page 45 and the corresponding description on pages 43 to 46, the disclosure of which is hereby incorporated herein by reference. A plugging cycle may comprise the following steps: A test area of a continuous gold foil tape may be deposited on a pressure plate by a retaining device. A test element may be moved on the test area of the gold foil tape. The material of the gold foil may be equal to the material of contact surfaces of the test element according to the disclosure. A way of contact may be comparable to a way of insertion of the test element into the evaluation device. Subsequently the contact element may be moved away from the test area of the gold foil tape. The test area of the gold foil tape may be moved from the pressure plate, e.g., by a driving unit, and a subsequent test area of the gold foil tape may be deposited on the pressure plate. While the test area and the contact element are in contact the transition resistance between the contact elements and the test area of the gold foil may be determined.

In the endurance test shown in FIG. 5, the transition resistance may be determined at eight contact points of the test area and the contact element. FIG. 5 shows the transition resistance R in Ω as a function of plugging cycles z for contact elements having a conductive surface containing metallic ruthenium (curve 154) and, for comparison, for contact elements having a surface containing hard materials (curve 156). Curve 156 shows a run-in behavior and a rise of transition resistance as the number of plugging operations increases, whereas curve 154 shows no run-in behavior and an overall flat shape. In addition, the scattering behavior of the determined transition resistance is shown as dashed areas between minimal and maximal measurement values, for contact elements having a conductive surface containing metallic ruthenium (reference number 158) and, for comparison, for contact elements having a surface containing hard materials (reference number 160). Surprisingly, it was found that a contact surface containing metallic ruthenium ensures a low transition resistance and a high reproducibility of the transition resistance with little scatter.

Figure 6:
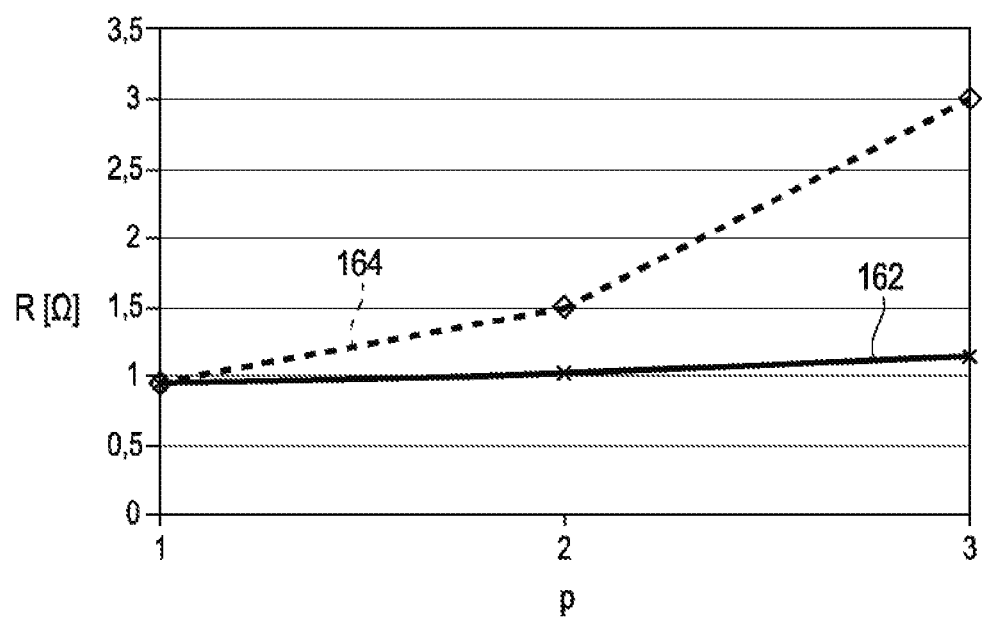
FIG. 6 shows transition resistance as a function of plugging operations.

FIG. 6 shows the transition resistance as a function of plugging operations p. In this endurance test, the same test element 116 may be inserted three times in sequence into the test element holder 114, wherein the contact surfaces 133 of the contact elements 132 of the test element holder 114 are provided with an electrically conductive surface 145 containing metallic ruthenium. Each time the transition resistance is determined (curve 162). For comparison, the test element 116 may be inserted three times in sequence into a test element holder having contact elements with hard material surfaces and each time the transition resistance is determined (curve 164). In case of using contact elements with hard material surfaces failures are observed at the third plugging operation. In case of using electrically conductive surface 145 containing metallic ruthenium functionality is ensured even at the third plugging operation. Thus, surprisingly, it was found that by using contact surfaces containing metallic ruthenium abrasion of the opposing softer contact surface is reduced compared to using contact surfaces containing hard material.

LIST OF REFERENCE NUMBERS 110 test element analysis system
112 evaluation device
114 test element holder
116 test element
117 contact surfaces
118 sample
120 spring element
122 measuring zone
124 sample application zone
126 transport zone
128 reagent layer
130 electrodes
132 contact element
133 contact surface
134 measuring device
136 measuring and evaluation electronics
138 printed circuit board
140 integrated circuit
142 electrically conductive contact surfaces
144 conductive path
145 electrically conductive surface
146 metallic ruthenium
148 metal part
150 conductive material
152 intermediate layer
154 curve
156 curve
158 scattering behavior
160 scattering behavior
162 curve
164 curve

What is claimed is:

1. A test element analysis system for an analytical examination of a sample comprising:
   a test element with at least one measurement zone and at least one electrically conductive contact surface; and
   an evaluation device with a test element holder for positioning the test element containing the sample, and a measuring device for measuring a change in the measuring zone of the test element, the change being characteristic for an analyte, wherein
   the test element holder contains contact elements with contact surfaces which allow an electrical contact between the contact surfaces of the test element and the contact surfaces of the test element holder,
   the contact surfaces of the contact elements of the test element holder are provided with an electrically conductive surface containing metallic ruthenium,
   the test element holder comprises at least one metal part containing the contact elements with the contact surfaces,
   the metal part comprises at least one conductive material other than ruthenium,
   the conductive material, in the region of the contact elements, is fully or partially coated with ruthenium, and
   the electrically conductive contact surfaces of the test element are softer than ruthenium.

2. The test element analysis system of claim 1, where in the sample is a body fluid.

3. The test element analysis system of claim 1, wherein the conductive material comprises copper.

4. The test element analysis system of claim 1, wherein the ruthenium is applied by galvanic coating, directly or indirectly onto the conductive material.

5. The test element analysis system of claim 1, wherein the metal part comprises one or more contact portions electrically connected to at least one electronic component of the evaluation device, wherein the one or more contact portions remain free of ruthenium.

6. The test element analysis system of claim 1, wherein the metal part is a punched press-bending part or a punched deep-drawn part.

7. The test element analysis system of claim 1, wherein the electrically conductive contact surfaces comprise one or both of electrodes or conductive paths.

8. The test element analysis system of claim 1, wherein the electrically conductive contact surfaces of the test element are fully or partially made of gold.

9. A method for manufacturing a test element analysis system according to claim 1, the method comprising the following steps:
   a) providing the contact elements having the electrically conductive surface containing metallic ruthenium; and
   b) electrically connecting the contact elements with at least one electronic component of the evaluation device,
   wherein step a) comprises providing at least one metal part containing the contact elements with contact surfaces, wherein the metal part is made of at least one conductive material other than ruthenium, wherein step a) further comprises fully or partially coating the conductive material, in the region of the contact elements, with ruthenium.

* * * * *